(12) United States Patent
Adamski et al.

(10) Patent No.: US 9,562,817 B2
(45) Date of Patent: Feb. 7, 2017

(54) MANIPULATION DEVICE WITH FORCE READ-OUT

(71) Applicants: Julie Adamski, Gilbertsville, PA (US); Dennis Adamski, Gilbertsville, PA (US); Stephanie Potter, Bethlehem, PA (US); John Briscoe, Gaylordsville, CT (US); Jillian Sloand, Bethlehem, PA (US); Benjamin Hotz, Far Hills, NJ (US); Daniel Rosen, Caldwell, NJ (US)

(72) Inventors: Julie Adamski, Gilbertsville, PA (US); Dennis Adamski, Gilbertsville, PA (US); Stephanie Potter, Bethlehem, PA (US); John Briscoe, Gaylordsville, CT (US); Jillian Sloand, Bethlehem, PA (US); Benjamin Hotz, Far Hills, NJ (US); Daniel Rosen, Caldwell, NJ (US)

(73) Assignee: Perfect Touch Technologies, LLC, Gilbertsville, PA (US)

( * ) Notice: Subject to any disclaimer, the term of this patent is extended or adjusted under 35 U.S.C. 154(b) by 154 days.

(21) Appl. No.: 14/243,258

(22) Filed: Apr. 2, 2014

(65) Prior Publication Data

US 2015/0285696 A1    Oct. 8, 2015

(51) Int. Cl.
*G01L 5/00* (2006.01)
*A61B 5/00* (2006.01)
(Continued)

(52) U.S. Cl.
CPC .......... *G01L 5/0038* (2013.01); *A61B 5/0053* (2013.01); *A61B 5/6806* (2013.01); *A61B 5/6823* (2013.01);
(Continued)

(58) Field of Classification Search
CPC ......... G01L 1/2206; G01L 1/26; G01L 5/0038
See application file for complete search history.

(56) References Cited

U.S. PATENT DOCUMENTS

| | | | | | |
|---|---|---|---|---|---|
| 1,558,666 | A | * | 10/1925 | Brewer | .................. A63B 60/40 473/518 |
| 2,077,202 | A | * | 4/1937 | Barrie | ........................ A01J 1/00 119/14.22 |

(Continued)

OTHER PUBLICATIONS

Interlink Electronics. Force Sensing Resistor Integration Guide and Evaluation Parts Catalog: 400 Series Evaluation Parts With Suggested Electrical Interfaces. Published online Nov. 23, 2009. Accessed online at <https://web.archive.org/web/20091123085412/http://www.sparkfun.com/datasheets/Sensors/Pressure/fsrguide.pdf>.*

(Continued)

*Primary Examiner* — Lisa Caputo
*Assistant Examiner* — Punam Roy
(74) *Attorney, Agent, or Firm* — Joseph E. Maenner; Maenner & Associates, LLC

(57) ABSTRACT

A manipulation and force measuring device includes a planar force sensing resistor, a protective material surrounding the resistor, and an outer material surrounding the protective material. A first strap extends outwardly from the outer material. The first strap has one of a hook and loop fastener disposed thereon. A second strap extends outwardly from the outer material, distal from the first strap. The second strap has the other of the hook and loop fastener disposed thereon. A processor is attached to one of the first strap and the second strap. The processor is electronically connected to the resistor. A loop extends outwardly from the outer material. The loop is located proximate to the first strap. A method of using the device is also disclosed.

11 Claims, 14 Drawing Sheets

(51) Int. Cl.
*G01L 1/20* (2006.01)
*A61B 5/22* (2006.01)

(52) U.S. Cl.
CPC .............. *A61B 5/6843* (2013.01); *G01L 1/20* (2013.01); *A61B 5/225* (2013.01); *A61B 2505/01* (2013.01); *A61B 2562/0247* (2013.01)

(56) References Cited

U.S. PATENT DOCUMENTS

| | | | | |
|---|---|---|---|---|
| 3,413,000 | A * | 11/1968 | Alkonis | A41D 19/01547 2/161.6 |
| 3,843,126 | A * | 10/1974 | Bandy | A63B 67/10 2/16 |
| 3,888,482 | A * | 6/1975 | Starrett | A63B 69/0002 473/458 |
| 4,144,877 | A * | 3/1979 | Frei | A61B 5/6806 307/400 |
| 4,337,780 | A * | 7/1982 | Metrick | A61B 5/225 600/487 |
| 4,586,387 | A * | 5/1986 | Morgan | G01L 5/223 2/160 |
| 4,617,684 | A * | 10/1986 | Green | A41D 13/082 2/16 |
| 4,958,384 | A * | 9/1990 | McCrane | A41D 19/01582 2/161.6 |
| 5,012,817 | A * | 5/1991 | Zeilinski | A61B 5/225 600/557 |
| 5,149,085 | A * | 9/1992 | Sanchez | A63B 23/14 473/450 |
| 5,188,356 | A * | 2/1993 | Furr | A63B 69/0071 128/880 |
| 5,368,042 | A * | 11/1994 | O'Neal | A61B 5/0006 128/905 |
| 5,441,413 | A | 8/1995 | Kumar | |
| 5,626,615 | A | 5/1997 | Keller et al. | |
| 5,733,201 | A * | 3/1998 | Caldwell | A63B 71/146 2/161.2 |
| 5,911,693 | A * | 6/1999 | Prochazka | A61B 5/225 600/587 |
| 6,244,271 | B1 * | 6/2001 | Turner | A61F 5/37 128/869 |
| 6,757,915 | B2 * | 7/2004 | Sidlo | A63B 71/14 2/16 |
| 6,836,744 | B1 * | 12/2004 | Asphahani | A43D 1/02 377/24.2 |
| 6,931,666 | B1 * | 8/2005 | Brady | A41D 13/08 2/16 |
| 7,101,287 | B1 * | 9/2006 | Wagner | A63B 69/3608 473/151 |
| 8,029,414 | B2 * | 10/2011 | Ingvast | A61H 1/0288 482/4 |
| 8,162,782 | B2 * | 4/2012 | Chen | A63B 69/0071 473/422 |
| 8,235,927 | B2 * | 8/2012 | Bauerfeind | A61F 5/0118 602/20 |
| 8,333,104 | B2 * | 12/2012 | Oberleitner | A63B 24/0021 73/12.04 |
| 8,574,135 | B2 * | 11/2013 | Chen | A63B 69/0086 473/422 |
| 8,702,634 | B2 * | 4/2014 | Crompton | A61F 5/0118 128/879 |
| 9,028,259 | B2 * | 5/2015 | Centen | G09B 23/288 434/265 |
| 9,192,335 | B2 * | 11/2015 | Linderman | A61B 5/6806 |
| 9,192,523 | B2 * | 11/2015 | Robson | A61F 13/104 |
| 2002/0178830 | A1 * | 12/2002 | Kazerooni | B65G 43/00 73/760 |
| 2003/0009087 | A1 * | 1/2003 | Keirsbilck | A61B 5/01 600/300 |
| 2003/0138761 | A1 * | 7/2003 | Pesnell | A63B 59/20 434/247 |
| 2006/0025690 | A1 * | 2/2006 | Guigne | A61B 5/6806 600/459 |
| 2007/0276303 | A1 | 11/2007 | Jenner, Jr. | |
| 2007/0289379 | A1 * | 12/2007 | You | G01L 1/205 73/379.03 |
| 2009/0070917 | A1 * | 3/2009 | Shoemaker | A41D 19/01582 2/161.1 |
| 2009/0099997 | A1 * | 4/2009 | Hubbard | G05G 1/42 706/54 |
| 2010/0228166 | A1 * | 9/2010 | Centen | A61H 31/004 601/41 |
| 2011/0302694 | A1 * | 12/2011 | Wang | A61B 5/103 2/160 |
| 2012/0089054 | A1 * | 4/2012 | Centen | G09B 23/288 601/41 |
| 2012/0266358 | A1 * | 10/2012 | Yuen | A61B 5/7475 2/162 |
| 2013/0197399 | A1 * | 8/2013 | Montgomery | A61B 5/1121 600/595 |
| 2013/0219585 | A1 * | 8/2013 | Bergelin | B25J 9/0006 2/160 |
| 2013/0219586 | A1 * | 8/2013 | Ihrke | B25J 15/08 2/160 |
| 2013/0333094 | A1 * | 12/2013 | Rogers | A41D 19/015 2/161.7 |
| 2014/0135666 | A1 * | 5/2014 | Butler | A61H 31/005 601/41 |
| 2014/0330087 | A1 * | 11/2014 | Succi | A61B 8/06 600/301 |
| 2015/0359457 | A1 * | 12/2015 | Blumenthal | A61B 5/103 73/172 |
| 2016/0018892 | A1 * | 1/2016 | Gu | G06F 3/016 345/156 |

OTHER PUBLICATIONS

Nussey, John. "What you should know about Arduino pressure, force, and load sensors." Arduino for Dummies. Published online Jan. 15, 2014. Accessed online at <www.dummies.com>.*
K. Dellimore et al., "Development of a diagnostic glove for unobtrusive measurement of chest compression force and depth during neonatal CPR," 2013 35th Annual International Conference of the IEEE Engineering in Medicine and Biology Society (EMBC), Osaka, 2013, pp. 350-353.*
Faculty of Engineering, "Engineering students develop life-saving CPR Glove," Daily News. McMaster University. Feruary 9, 2007.*
"Inventors of CPR Glove win U.S. prize," Hamilton—The Canadian Press, The Globe and Mail. Nov. 3, 2007.*
"Media Advisory-OCE Gives CPRGlove a Helping Hand to Gain Market Viability," Marketwire. Ontario Centers of Excellence Inc. Jan. 2, 2008.*
Tuttle, Neil, et al. "Design and Construction of a Novel Low-Cost Device to Provide Feedback on Manually Applied Forces", Journal of Orthopaedic & Sports Physical Therapy Mar. 2011, vol. 41, No. 3, pp. 174-179, A1-11.
http://sensoglove.com/. printed Apr. 9, 2014. 5 pages.
Extremity Drop/Speeder Board. printed Apr. 9, 2014. www.thulitables.com.
www.activator.com. printed Apr. 9, 2014. 2 pages.
www.hogganhealth.net/micfofet2.php. printed Apr. 9, 2014. 2 pages.

* cited by examiner

MANIPULATION DEVICE WITH FORCE READ-OUT

BACKGROUND OF THE INVENTION

Presently, when a healthcare provider, such as a chiropractor, a physical therapist, or a physician, applies a force to a region on a patient's body, the provider has no clear indication of how much force is actually being applied. If the provider applies too much force, the provider may inadvertently aggravate the patient's symptoms or cause bodily harm. Currently, healthcare providers use subjective terms such as mild or moderate when measuring force. It would be beneficial to provide a device that provides real time objective information and stored data to be analyzed and documented later about the amount of force that is being applied to the patient by the health care provider.

BRIEF SUMMARY OF THE INVENTION

Briefly, the present invention provides a manipulation and force measuring device comprising a planar force sensing resistor, a protective material surrounding the resistor, and an outer material surrounding the protective material. A first strap extends outwardly from the outer material. The first strap has one of a hook and loop fastener disposed thereon. A second strap extends outwardly from the outer material, distal from the first strap. The second strap has the other of the hook and loop fastener disposed thereon. A processor is attached to one of the first strap and the second strap. The processor is electronically connected to the resistor. A loop extends outwardly from the outer material. The loop is located proximate to the first strap. A method of operating the device is also provided.

Further, the present invention provides a spinal manipulation glove comprising a palm portion having a first planar force sensing resistor, a first protective material surrounding the first resistor, and a first outer material surrounding the first protective material. A dorsal portion has a second planar force sensing resistor, a second protective material surrounding the second resistor, and a second outer material surrounding the second protective material. A wrist portion having a processor is coupled to the dorsal portion. The processor is electronically connected to the first resistor and to the second resistor. A method of operating the glove is also provided.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
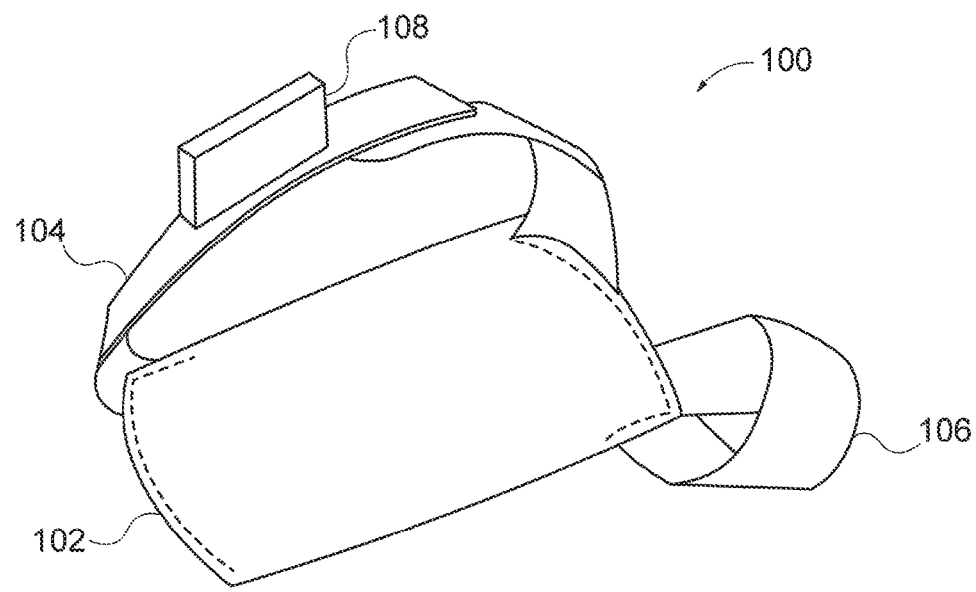
FIG. 1 is a perspective view of a manipulation device according to a first exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "glove" is a device that covers the hand of the wearer. Such a glove may have fingers or be fingerless. Further, the term "force" can be defined by objective measuring numbers such as pounds or millimeters of mercury (mmHg). Manipulation can be interpreted to further include pressure, thrust, mobilization and/or manipulation. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

The inventive force measuring device for healthcare providers is used to objectively measure the amount of force applied to a patient, such as during mobilizations, manipulations, and during CPR to allow for reproducibility, consistency and future studies of optimal pressure for selected population for which force, thrust or pressure is required.

Figure 2:
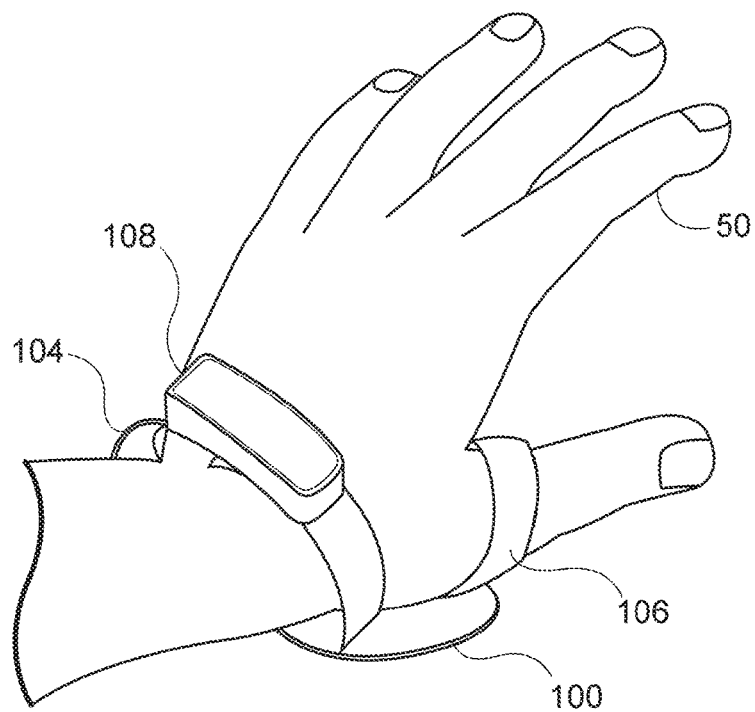
FIG. 2 is a perspective view of the manipulation device shown in FIG. 1, worn by a user.
Figure 3:
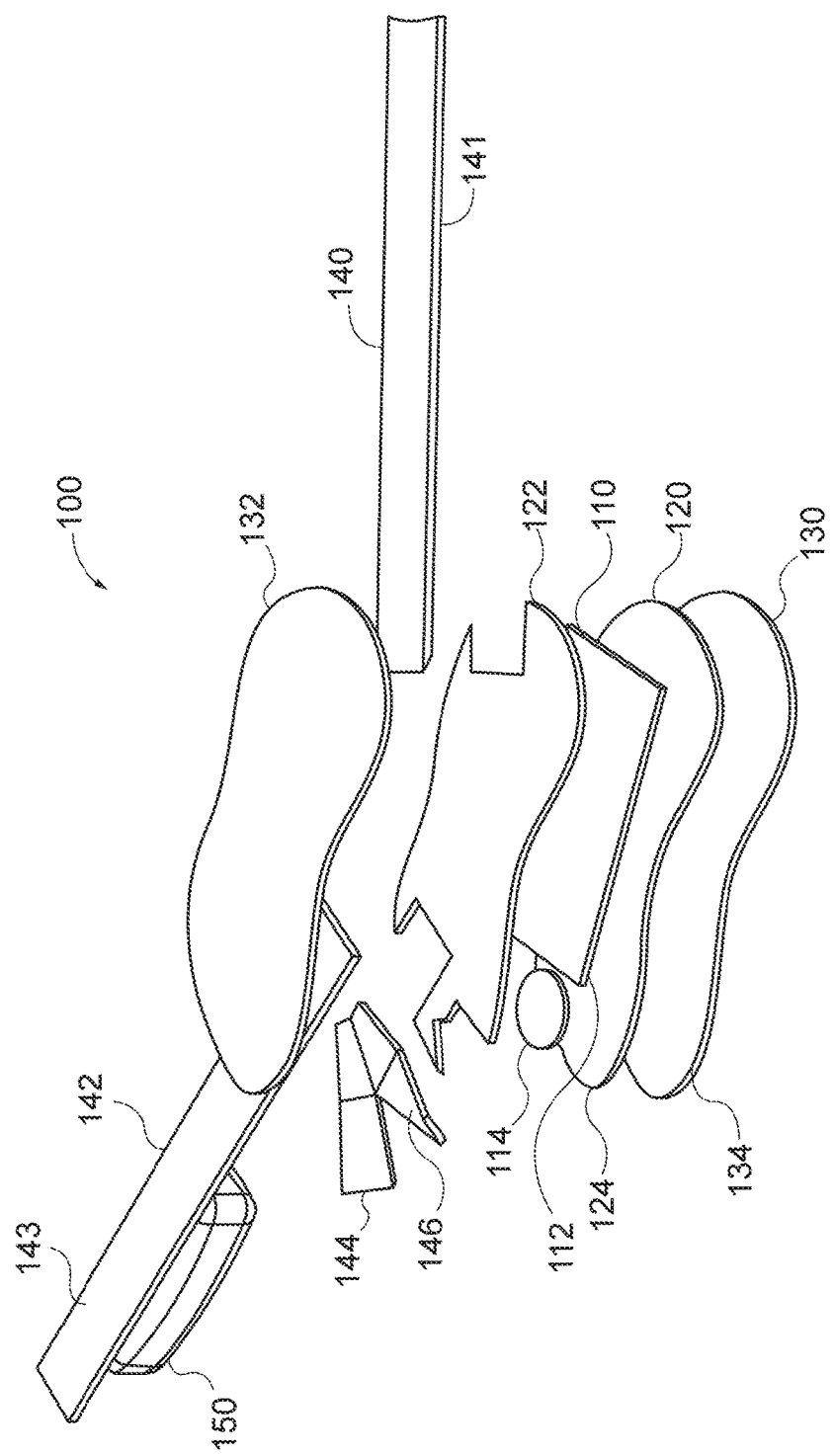
FIG. 3 is an exploded perspective view of the manipulation device shown in FIG. 1.

Referring to FIGS. 1-3, a first exemplary embodiment of a manipulation device 100 according to a first exemplary embodiment of the present invention is shown. When in use, device 100 is removably attached to the hand 50 of a healthcare provider, such as, for example, a physical therapist, a chiropractor, a physician, a student learning how to manipulate a patient, or other such healthcare professional. Device 100 measures and displays the amount of force that the healthcare provider is applying to a patient in real-time, so that the healthcare provider knows how much force is being applied, and can reduce the amount of force if the force is excessive, or apply additional force if the force is too low. The amount and duration of the applied force can be stored for later review and/or documentation.

Device 100 includes a force sensing resistor assembly 102, a wrist strap 104, a thumb strap 106, and a processor/transmitter 150. Wrist strap 104 and thumb strap 106 are attached to resistor assembly 102, while processor/transmitter 108 is attached to wrist strap 104. Device 100 can be worn on user's hand 50 as shown in FIG. 2. While device 100 is shown in FIG. 2 as being worn on the left hand, the construction of device 100 allows device 100 to be worn on the right hand (not shown).

Figure 2A:
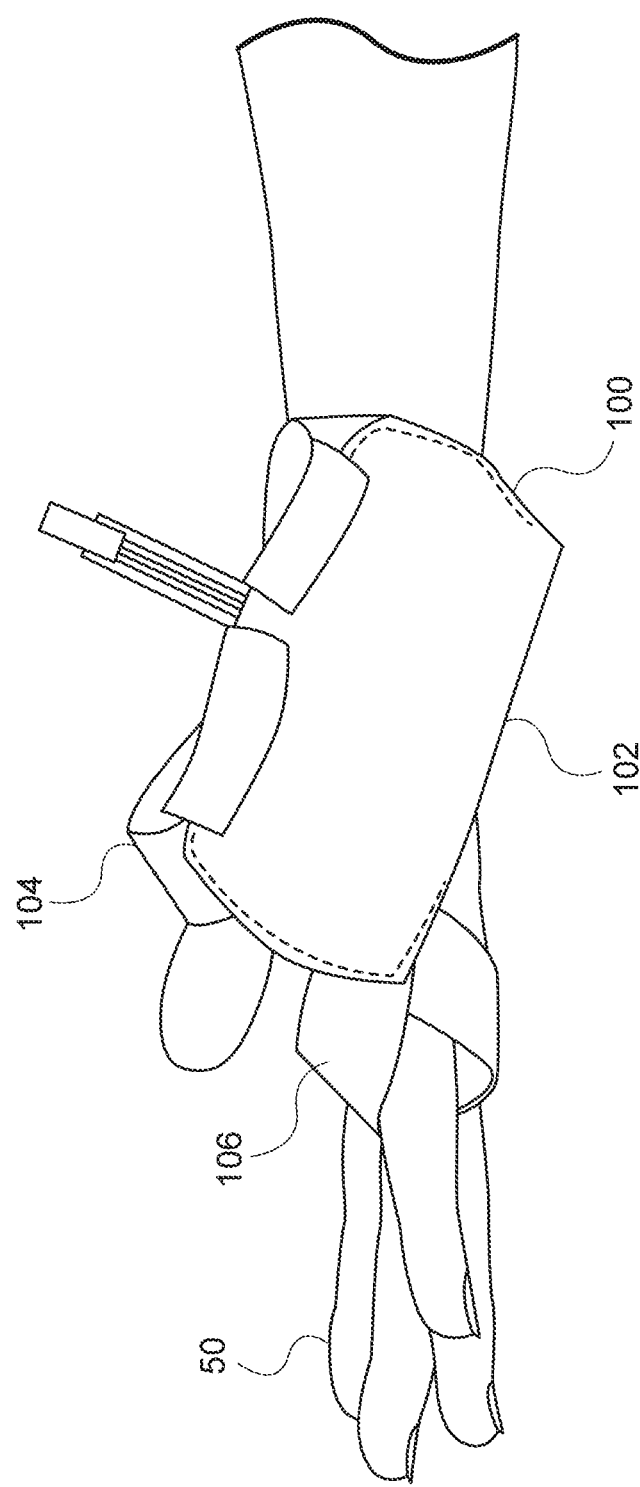
FIG. 2A is a perspective view of the manipulation device shown in FIG. 1, worn on a user in a different configuration than worn in FIG. 2.
Figure 2B:
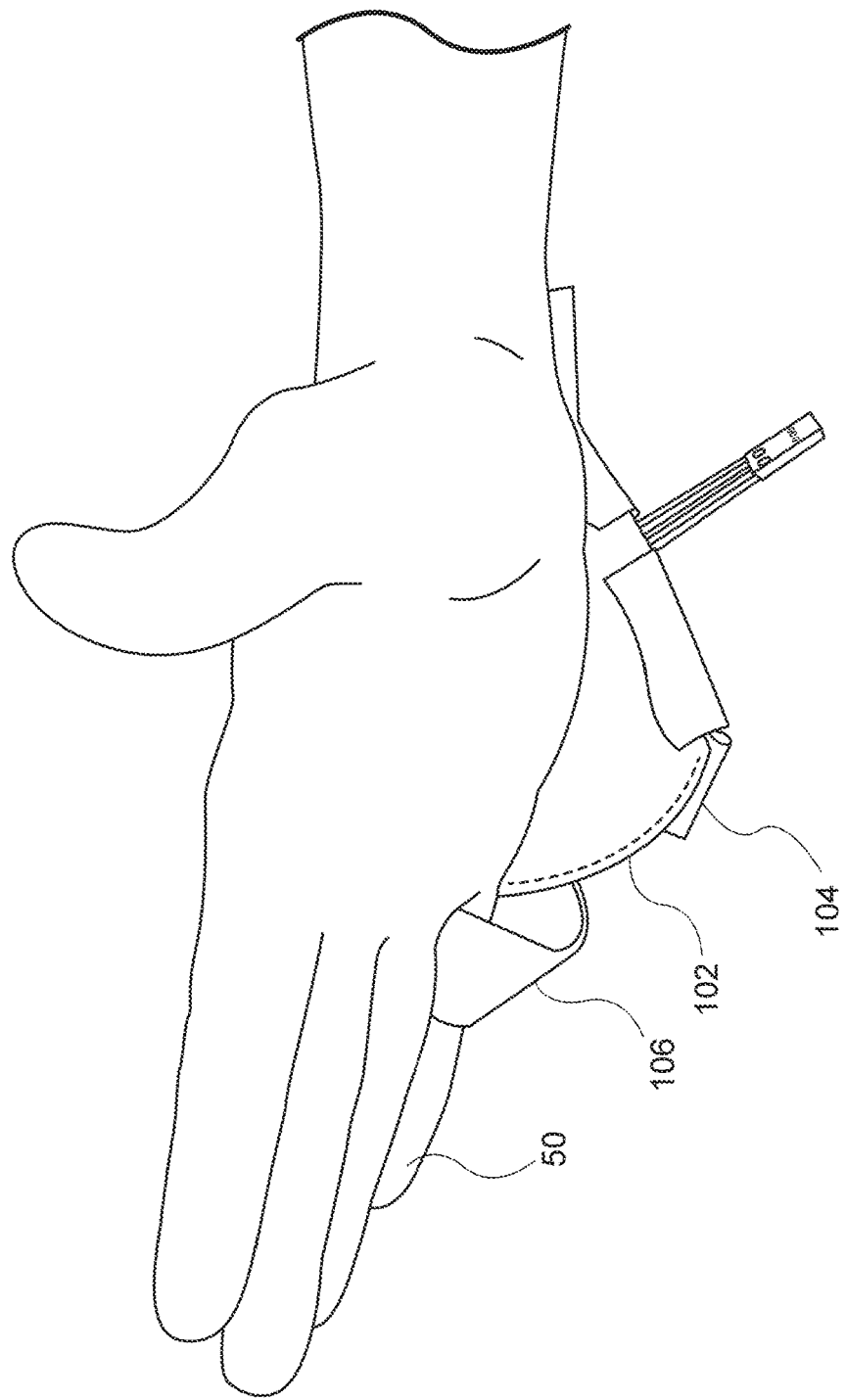
FIG. 2B is a perspective view of the manipulation device shown in FIG. 1, worn on a user in the same configuration as worn in FIG. 2A, but viewed from a different angle.

Device 100 can also be worn by placing the force sensing resistor 102 against the ulnar aspect of the hand 50 with thumb strap 106 now on digit 5 (pinky finger) and wrist strap 104 either wrapped around or, alternatively, not wrapped around the writs, as shown in FIGS. 2A and 2B. An exemplary use of device 100 in this configuration is for a desired mobilization or manipulation.

The construction of device 100 allows device 100 to be used both palmar or ulnar aspect on hand and both left and right hand. Device 100 can also be used by not using straps 104, 106, but by placing the force sensing resistor assembly 102 against a desired location on the patient so that one or more digits of user's hand 50 can apply force through device 100 if desired by the user.

Figure 2C:
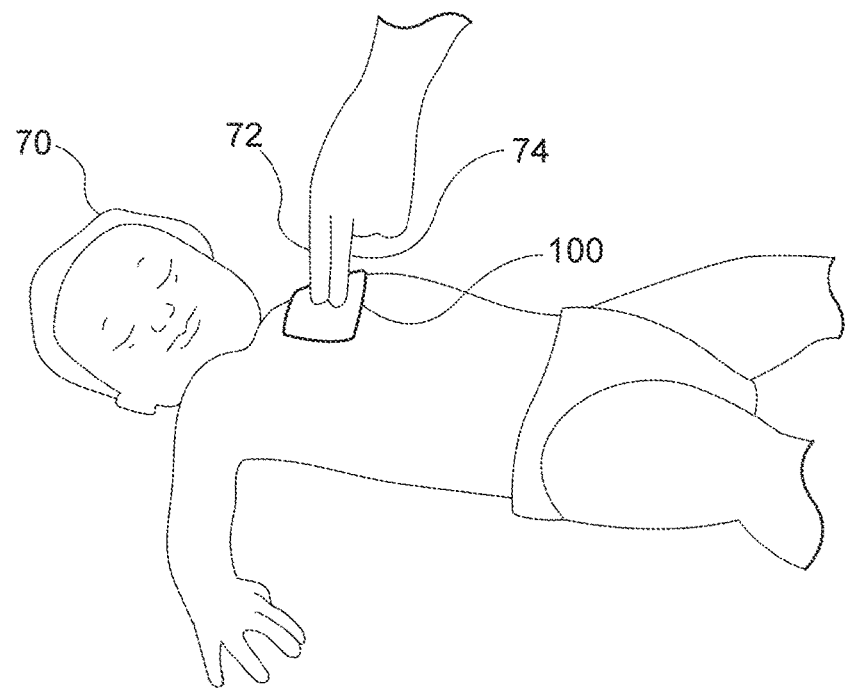
FIG. 2C is a perspective view of the use of the manipulation device of FIG. 1 to perform cardio pulmonary resuscitation (CPR) on an infant.
Figure 2D:
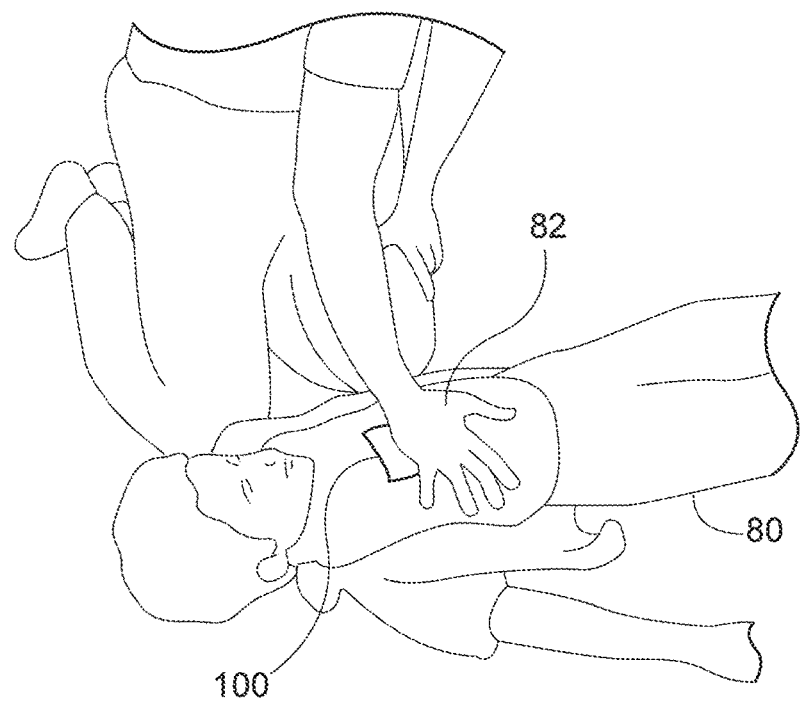
FIG. 2D is a perspective view of the use of the manipulation device of FIG. 1 to perform CPR on a child.
Figure 2E:
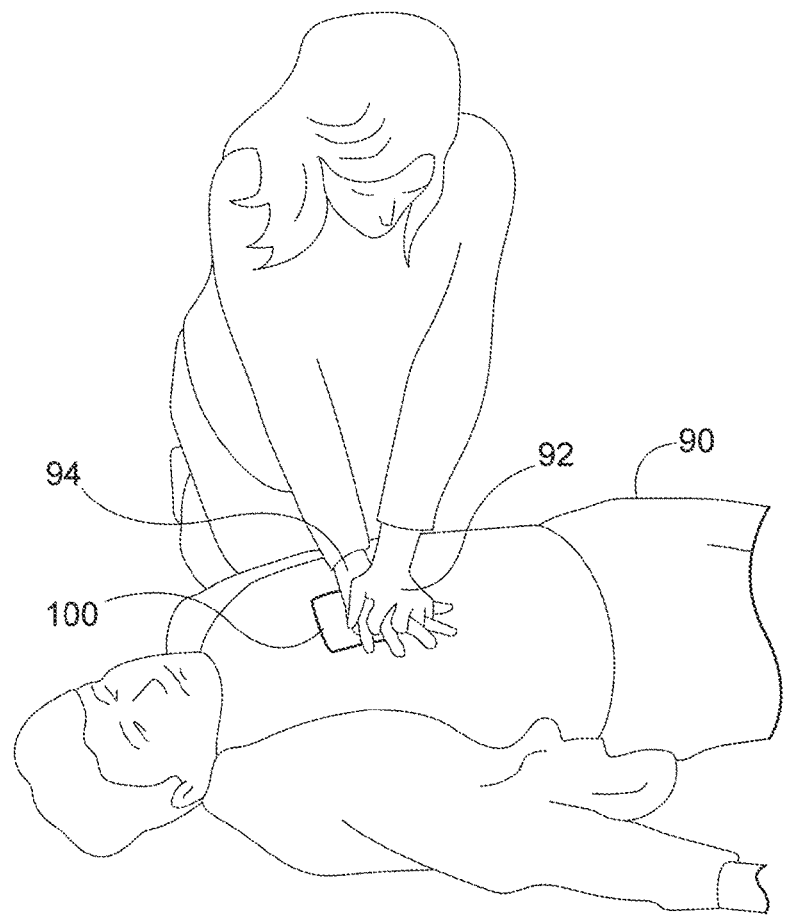
FIG. 2E is a perspective view of the use of the manipulation device of FIG. 1 to perform CPR on an adult.

Device 100 can be used for mobilization/manipulation, two-finger cardio pulmonary resuscitation (CPR) on an infant, one-hand CPR for a child, or two-hand CPR for an adult. FIG. 2C shows the use of device 100 used in performing CPR on an infant 70, by placing device 100 on the infant's chest and pressing down on the chest, through device 100, with two fingers 72, 74. FIG. 2D shows the use of device 100 used in performing CPR on a child 80, by placing device 100 on the child's chest and pressing down on the chest, through device 100, with one hand 82. FIG. 2E shows the use of device 100 used in performing CPR on an adult 90, by placing device 100 on the adult's chest and pressing down on the chest, through device 100, with two hands 92, 94.

Device 100 uses a planar force sensing resistor 110 that changes resistance due to deformation as a force is applied to device 100. An exemplary resistor can be the model SEN-09376, manufactured by Karlsson Robotics. The change in resistance can be measured and correlated to the amount of force being applied to resistor 110, as is well known in the art.

As shown in the exploded view of device 100 in FIG. 3, force sensing resistor assembly 102 includes resistors 110, 112, 114, a protective material 120, and an outer material 130. Three planar force sensing resistors 110, 112, 114 are used in device 100, although those skilled in the art will recognize that more or less than three resistors can be used. If more than one resistor 110 is used, resistors, such as resistors 110, 112, 114 are electrically connected to each other in series, as is well known in the art. When the user attaches device 100 to his/her hand, resistor 110 is located along the thenar eminence of the user's hand.

Protective material 120 surrounds resistor 110. Protective material 120 includes a first layer 122 that is disposed on one side of resistor 110, and a second layer 124 that is disposed on an opposing side of resistor 110. Protective material 120 serves to give structure to resistor assembly 102 and to protect resistors 110, 112, 114. An exemplary protective material 120 is a high density foam.

Outer material 130 surrounds protective material 120. Outer material 130 includes a first layer 132 that is disposed on one side of resistor 110 and a second layer 134 that is disposed on the opposing side of resistor 110. An exemplary outer material 130 is a medical grade material, such as medical grade nylon.

Wrist strap 104 includes a first strap 140 that extends outwardly from outer material 130. First strap has one of a hook 141 and loop 143 fastener disposed thereon. A second strap 142 extends outwardly from outer material 130, distal from first strap 140. Second strap has the other of the hook 141 and loop 143 fastener disposed thereon. Straps 140, 142 are sufficiently long to allow first strap 140 to be releasably secured to second strap 140 around the wrist of the user. Straps 140, 142 can be constructed from an elastic material to allow wrist strap 104 to be adjusted based on the size of the user's wrist or for the comfort of the user.

Processor/transmitter 150 is attached to one of first strap 140 and second strap 142. As shown in FIG. 3, processor 150 is attached to second strap 142. Processor/transmitter 150 is electronically connected to resistor 110 by a flexible connection, such as wires (not shown). Any wires can be sewn into strap 142 to protect the wires and prevent the wires from being inadvertently pulled out from either processor/transmitter 150 or resistor 110.

Figure 4:
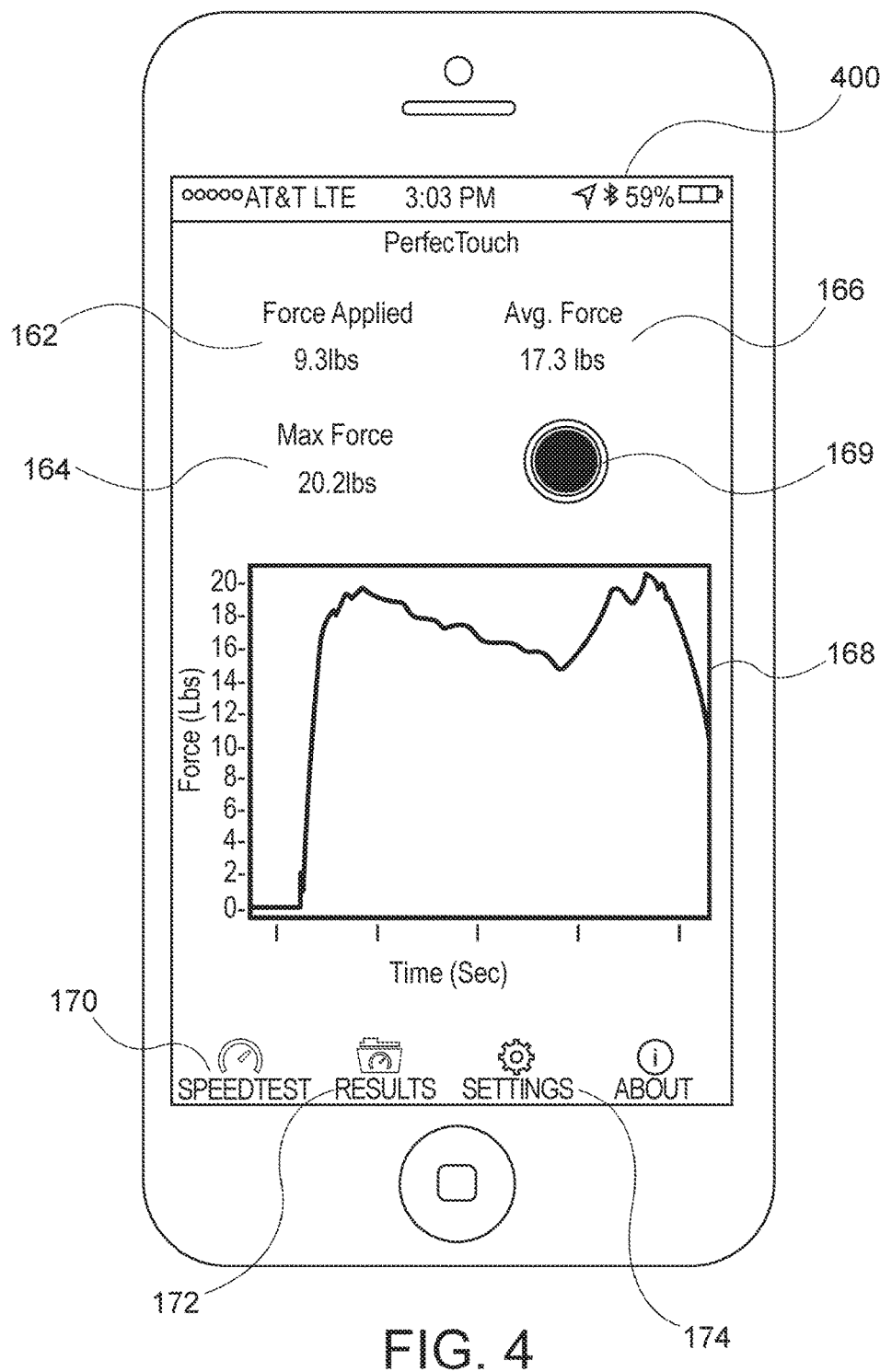
FIG. 4 is an exemplary graphical user interface ("GUI") of a force readout display for use with the manipulation device shown in FIG. 1.

Processor/transmitter 150 provides an electrical signal to resistor 110. As device 100 is being used, resistor 110 deflects, changing its electrical resistance. Processor/transmitter 150 receives the changed resistance in the form of a change in voltage, which is processed as a force being applied to resistor 110. Any electrical circuit that is known to be able to convert change in resistance into applied force can be used to electrically connect processor/transmitter 150 to resistor 110, and The applied force can be displayed on a display screen (not shown) on processor/transmitter 150. Alternatively, processor/transmitter 150 can include a radio frequency transmitter to transmit the force information to a remote receiver, such as a cell phone or other electronic data device. An exemplary receiver 160 is shown in FIG. 4.

Receiver 160 displays a graphical user interface ("GUI") 400 that includes discrete information about the force applied by device 100, such as, for example, the present force 162 being applied, the maximum force 164 that was applied during this particular session, and the average force 166 that was applied during this particular session. Also, receiver 160 can display a graph 168 showing how the force has been applied over a period of time. GUI 400 can be displayed directly on processor/transmitter 150 is processor/transmitter 150 is equipped with a display device. Alternatively, GUI 400 can be displayed on a remote electronic device if processor/transmitter 150 is equipped with a radio frequency transmitter.

Figure 5:
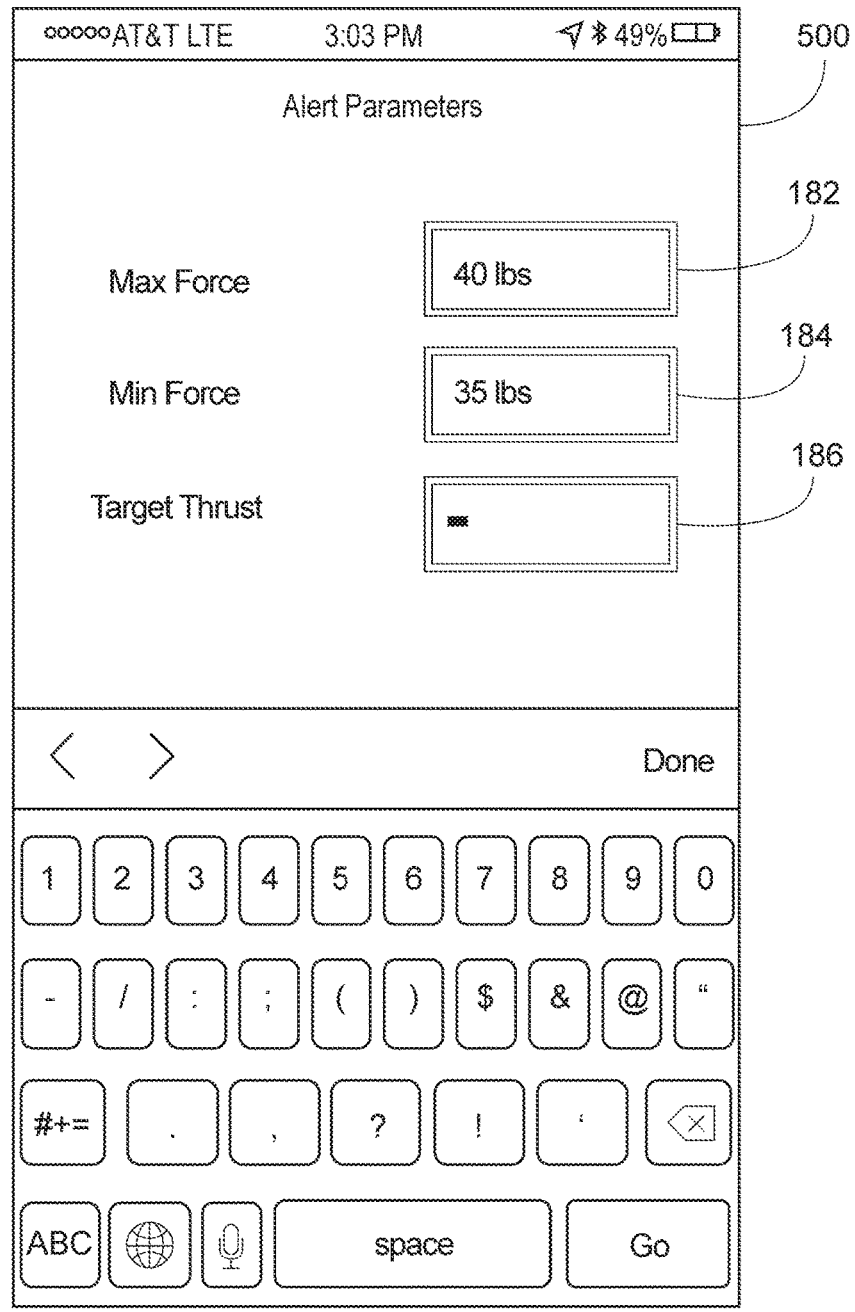
FIG. 5 is an exemplary GUI of alert parameters for use with the manipulation device shown in FIG. 1.
Figure 6:
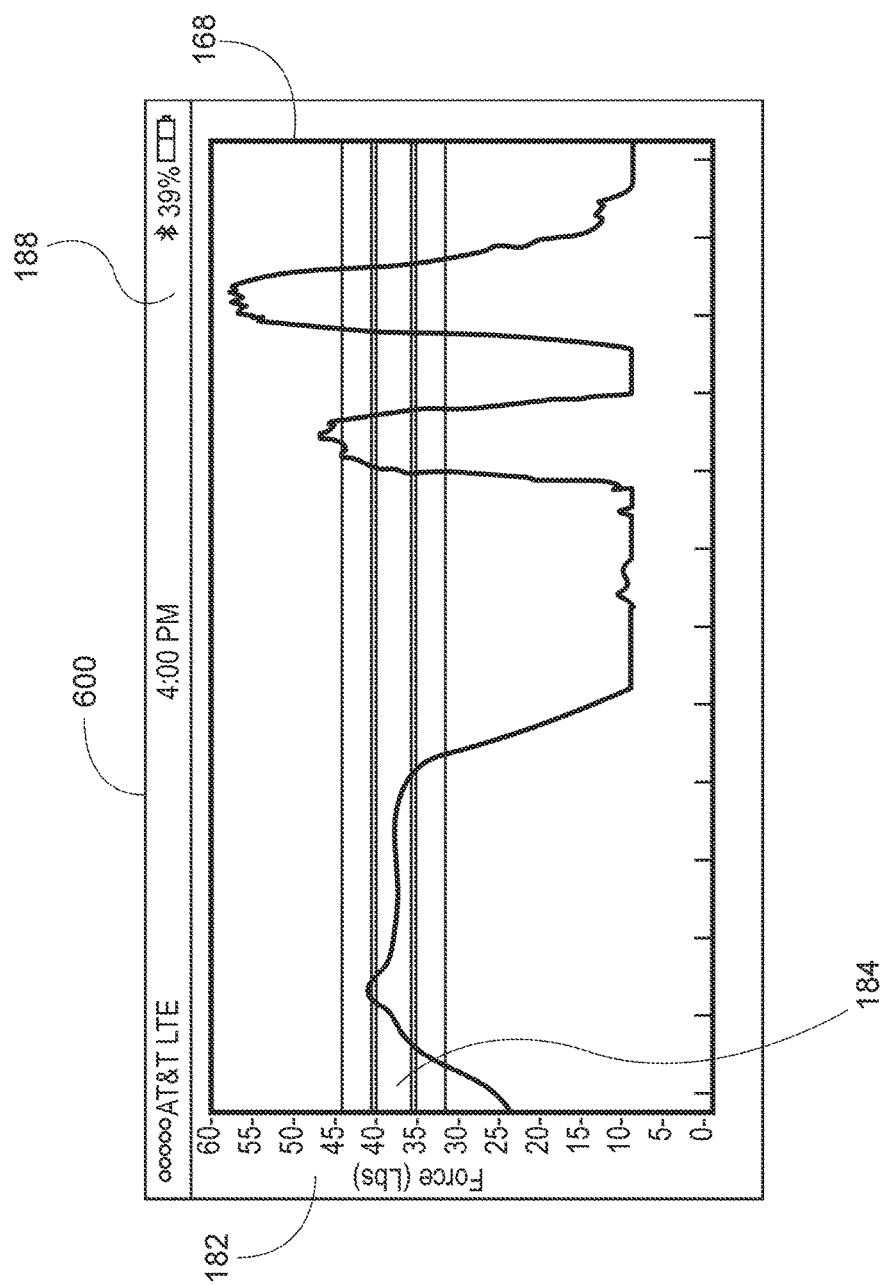
FIG. 6 is an exemplary GUI of a force readout display for use with the manipulation device shown in FIG. 1, incorporating the alert parameters from FIG. 5.

A recording button 169 records measurements taken over time and logs the measurements for later review. A "SPEED-TEST" icon 170 can generate a homepage. A "RESULTS" icon 172 can be pressed to display the results obtained from recording button 169. A "SETTINGS" icon 174 can be pressed to display appropriate settings and connection (i.e., Bluetooth, etc.) information. Additionally, "SETTINGS" icon 174 can be pressed to generate "Alert Parameters" GUI 500, shown in FIG. 5.

"Alert Parameters" GUI 500 allows the user to set a maximum force 182, a minimum force 184, and a target thrust 186 (if desired) for use with a patient (not shown). These parameters may be varied according to patient.

After the maximum force 182 and minimum force 184 parameters are set, GUI 600 displays maximum force 182 and minimum force 184 as straight lines across graph 168. The applied force values over time are superimposed onto graph 168 as line 188.

The force values and graphs shown in GUI 400, 500, 600 provide the user with objective values to target and observe the amount of force applied to the patient, rather than subjective values, such as "mild", "moderate", or "heavy," which can vary between users as well as patients. A user may be able to correlate the subjective values with objective force values. By way of example only, a "moderate" force may be in a range of between about 15 lbs and 25 lbs. A "mild" force may be less between about 2 lbs and about 15 lbs and a "heavy" force may be greater than 25 lbs.

Referring back to FIG. 3, thumb loop 106 extends outwardly from outer material 130. Loop 106 is located proximate to strap 142. Loop 106 can be constructed from a single material, or, as shown in FIG. 3, loop 106 can be constructed from a first loop material 144 and a second loop material 146 that are joined together. To allow the user's thumb to be inserted into thumb loop 106 such that thumb loop 106 can fit snugly onto the thumb of the user, thumb loop 106 can be manufactured from an elastic material.

Figure 7:
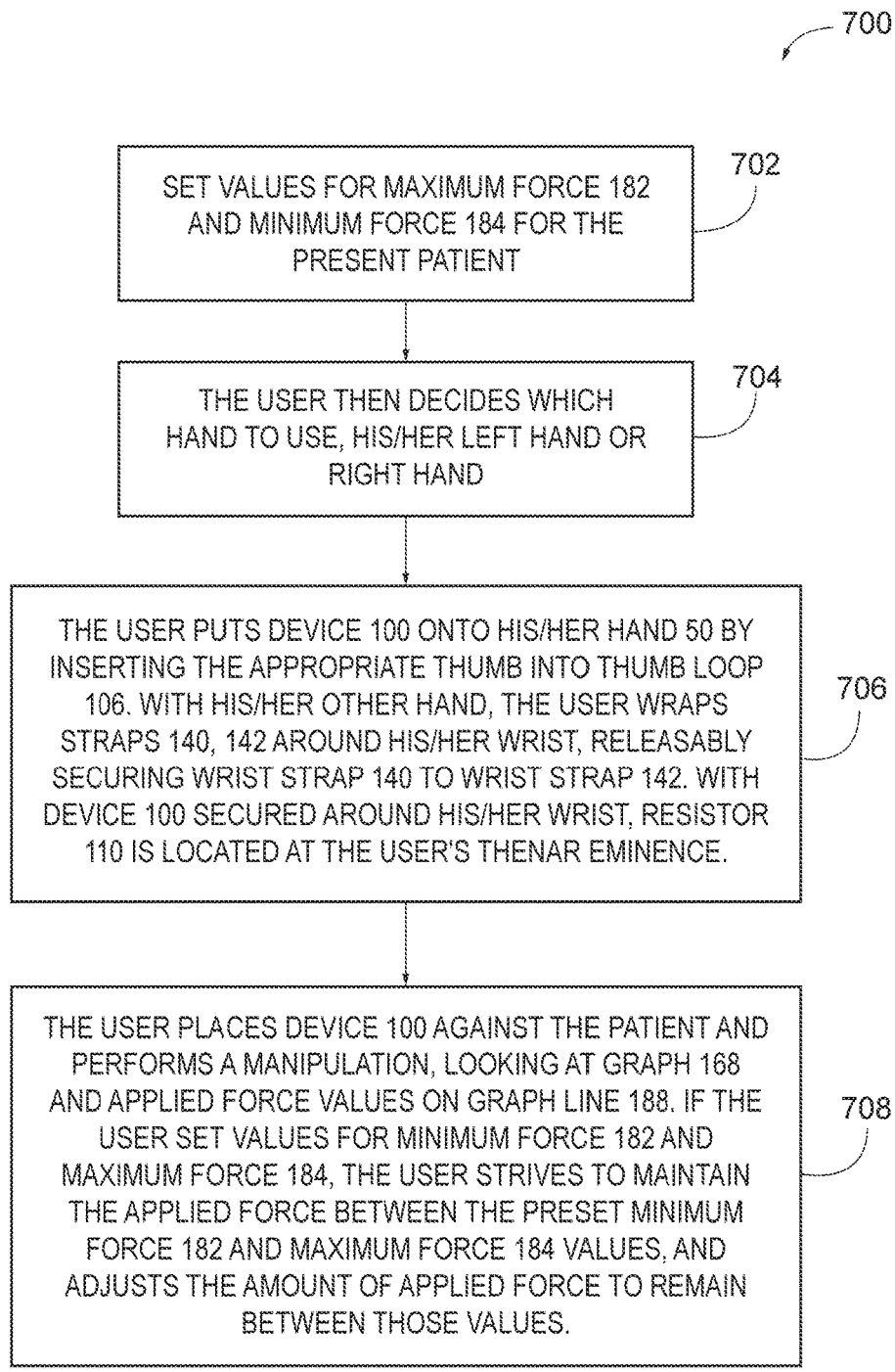
FIG. 7 is a flowchart illustrating an exemplary operation of the manipulation device shown in FIG. 1.

An exemplary operation of device 100 is illustrated in flow chart 700, shown in FIG. 7. To use device 100, in step 702, the user, if desired, can use GUI 500 to set values for maximum force 182 and minimum force 184 for the present patient. In step 704, the user then decides which hand to use, his/her left hand or right hand, and in step 706, the user puts device 100 onto his/her hand 50 by inserting the appropriate thumb into thumb loop 106. With his/her other hand, the user wraps straps 140, 142 around his/her wrist, releasably securing wrist strap 140 to wrist strap 142. With device 100 secured around his/her wrist, resistor 110 is located at the user's thenar eminence and hypothenar eminence.

In step 708, the user places device 100 against the patient and performs a manipulation, a mobilization, or a CPR thrust, looking at graph 168 and applied force values on graph line 188. If the user set values for minimum force 182 and maximum force 184, the user strives to maintain the applied force between the preset minimum force 182 and maximum force 184 values, and adjusts the amount of applied force to remain between those values. The user applies the force for whatever amount of time the user feels appropriate, or when the user feels that the patient has been properly manipulated, mobilized, or CPR performed.

Figure 8:
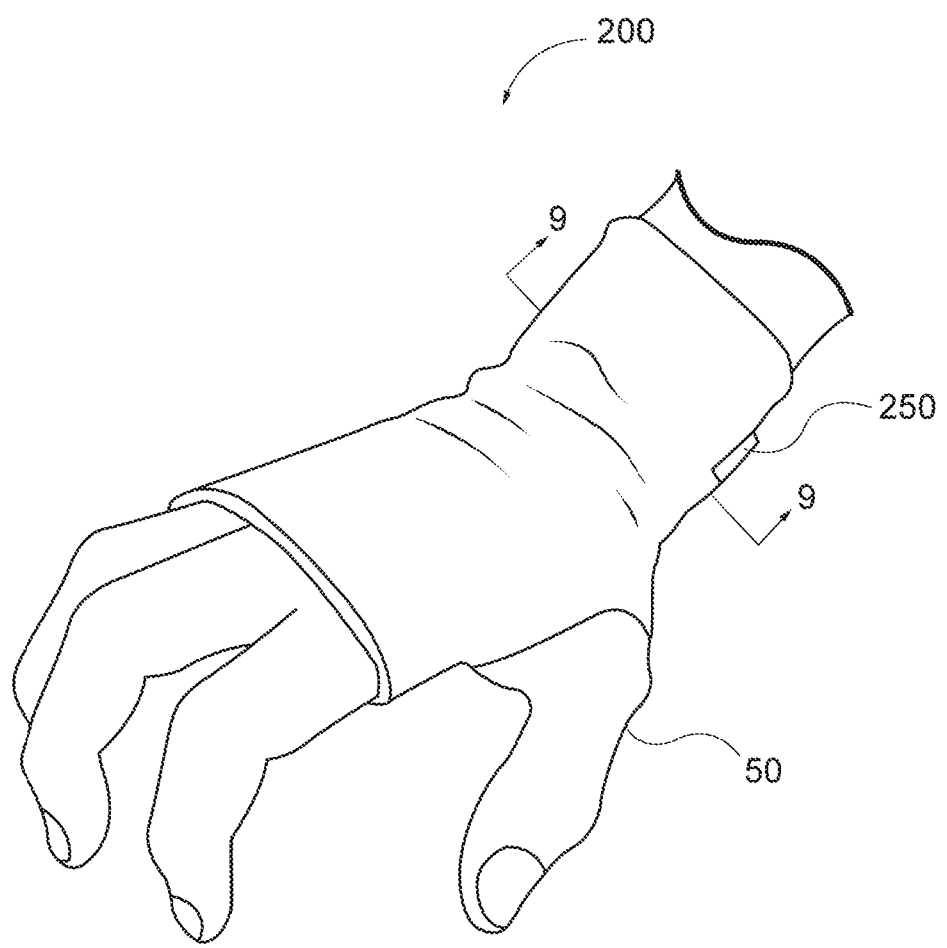
FIG. 8 is a perspective view of a manipulation device according to a second exemplary embodiment of the present invention, being worn by a user.
Figure 9:
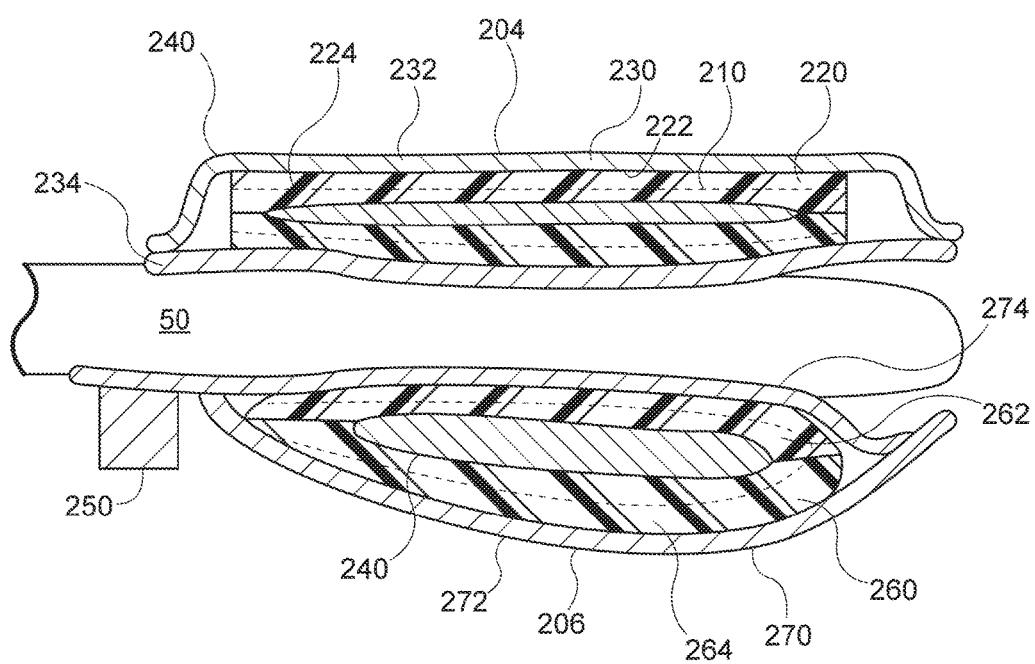
FIG. 9 is a sectional view of the device taken along lines 9-9 of FIG. 8.

Referring to FIGS. 8-9 a manipulation device 200 according to a second exemplary embodiment of the present invention is shown. Device 200 includes a fingerless glove 202 that can be worn on the user's hand 50 when performing spinal manipulations, mobilizations, or CPR thrusts. Because glove 202 is fingerless, glove 202 can be used on either the user's left hand or right hand.

As shown in FIG. 9, glove 202 includes a palm portion 204 having a first planar force sensing resistor 210. While a single resistor 210 is shown being used in device 200, those skilled in the art will recognize that more than one resistor 210 can be used. For example, an additional resistor (not shown) can be provided that corresponds to the fifth metacarpal, and/or the palm. If more than one resistor 210 is used, resistors are electrically connected to each other in series, as is well known in the art. When the user puts device 200 over his/her hand, resistor 210 is located along the thenar eminence and the hypothenar eminence of the user's hand.

A first protective material 220 surrounds first resistor 210. First protective material 220 includes a first layer 222 that is disposed on one side of resistor 210, and a second layer 224 that is disposed on an opposing side of resistor 210. Protective material 220 serves to give structure to palm portion 204 and to protect resistor 210. An exemplary protective material 220 is a high density foam.

A first outer material 230 surrounds first protective material 220. Outer material 230 includes a first layer 232 that is disposed on one side of resistor 210 and a second layer 234 that is disposed on the opposing side of resistor 210. An exemplary outer material 230 is a medical grade material, such as nylon. As shown in FIG. 9, first layer 232 can be integral with palm portion 204.

Glove 202 also includes a dorsal portion 206 that includes a second planar force sensing resistor 240. While a single resistor 240 is shown being used in device 200, those skilled in the art will recognize that more than one resistor 240 can be used. If more than one resistor 240 is used, resistors are electrically connected to each other in series, as is well known in the art. When the user puts device 200 over his/her hand, resistor 240 is located along the back of the user's wrist, and may possibly be not used to apply force to the patient. Resistor 240 is used when the user puts glove 202 onto the other hand, in which case resistor 240 will be located along the thenar eminence of the user's other hand.

A second protective material 260 surrounds second resistor 240. Second protective material 260 includes a first layer 262 that is disposed on one side of resistor 240, and a second layer 264 that is disposed on an opposing side of resistor 240. Protective material 260 serves to give structure to dorsal portion 206 and to protect resistor 240. An exemplary protective material 260 is a high density foam.

A second outer material 270 surrounds second protective material 260. Outer material 270 includes a first layer 272 that is disposed on one side of resistor 240 and a second layer 274 that is disposed on the opposing side of resistor 240. An exemplary outer material 270 is a medical grade material, such as nylon. As shown in FIG. 9, first layer 272 can be integral with dorsal portion 206.

Glove 202 also includes a wrist portion 208 having a processor/transmitter 250 coupled thereto. Processor/transmitter 250 is electronically connected to first resistor 210 and to second resistor 240. Similar to device 100, processor/transmitter 250 further comprises one of a visual display and a radio frequency transmitter. Further, similar to device 100, device 200 can have a visual display (not shown) physically attached to processor/transmitter 250, or, alternatively, can be linked via radio frequency to a remote device, such as device 160, shown in FIG. 4.

Figure 10:
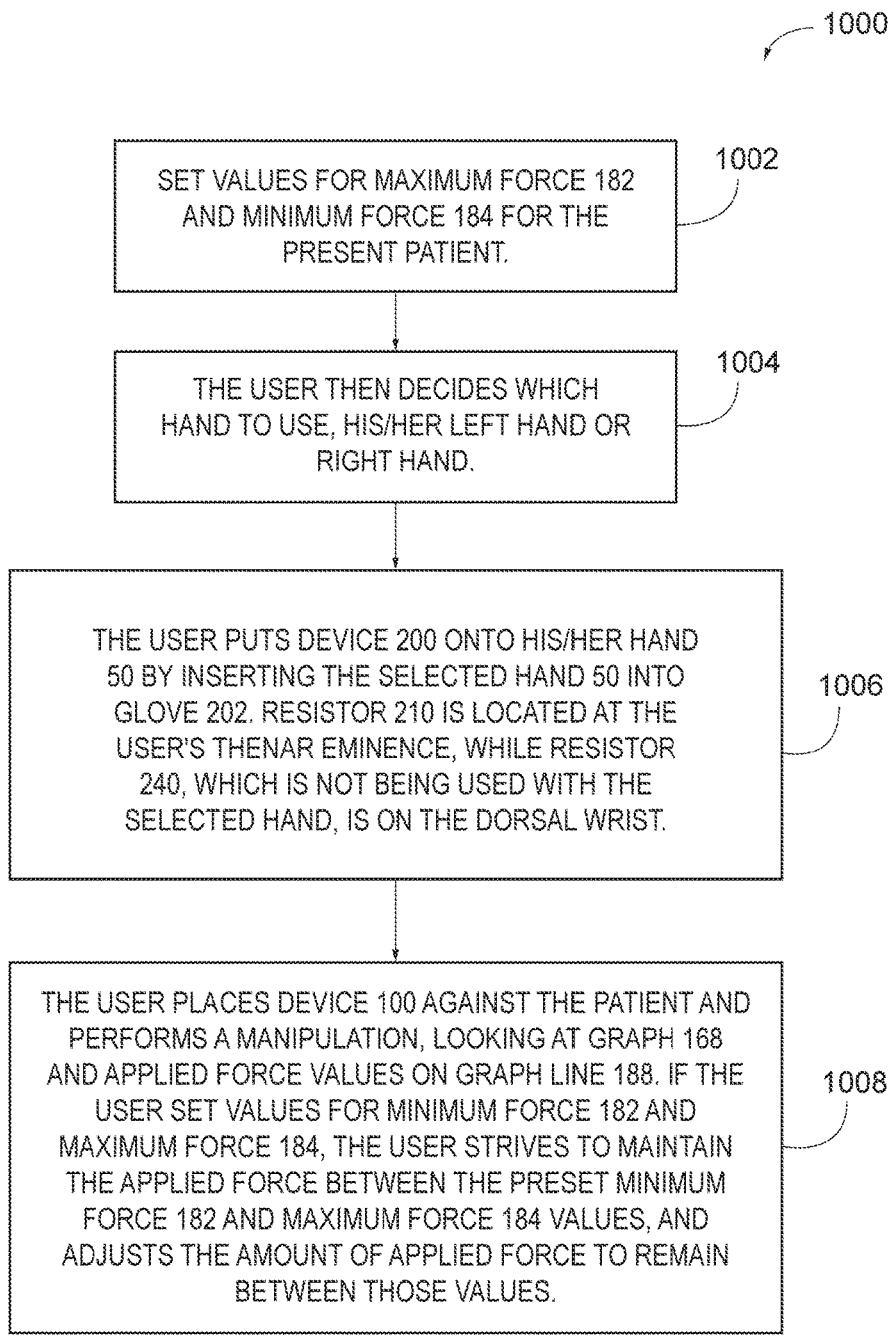
FIG. 10 is a flowchart illustrating an exemplary operation of the manipulation device shown in FIG. 8.

An exemplary operation of device 200 is illustrated in flow chart 1000, shown in FIG. 10. To use device 200, in step 1002, the user, if desired, can use GUI 500 to set values for maximum force 182 and minimum force 184 for the present patient. In step 1004, the user then decides which hand to use, his/her left hand or right hand, and in step 1006, the user inserts the selected hand 50 into glove 202. Resistor 210 is located at the user's thenar eminence and hypothenar eminence, while resistor 240, which is not being used with the selected hand, is on the dorsal wrist.

In step 1008, the user places device 200 against the patient and performs a manipulation, mobilization, or CPR thrust, looking at graph 168 and applied force values on graph line 188. If the user set values for minimum force 182 and maximum force 184, the user strives to maintain the applied force between the preset minimum force 182 and maximum force 184 values, and adjusts the amount of applied force to remain between those values. The user applies the force for whatever amount of time the user feels appropriate, or when the user feels that the patient has been properly manipulated, mobilized, or CPR force applied.

Figure 11:
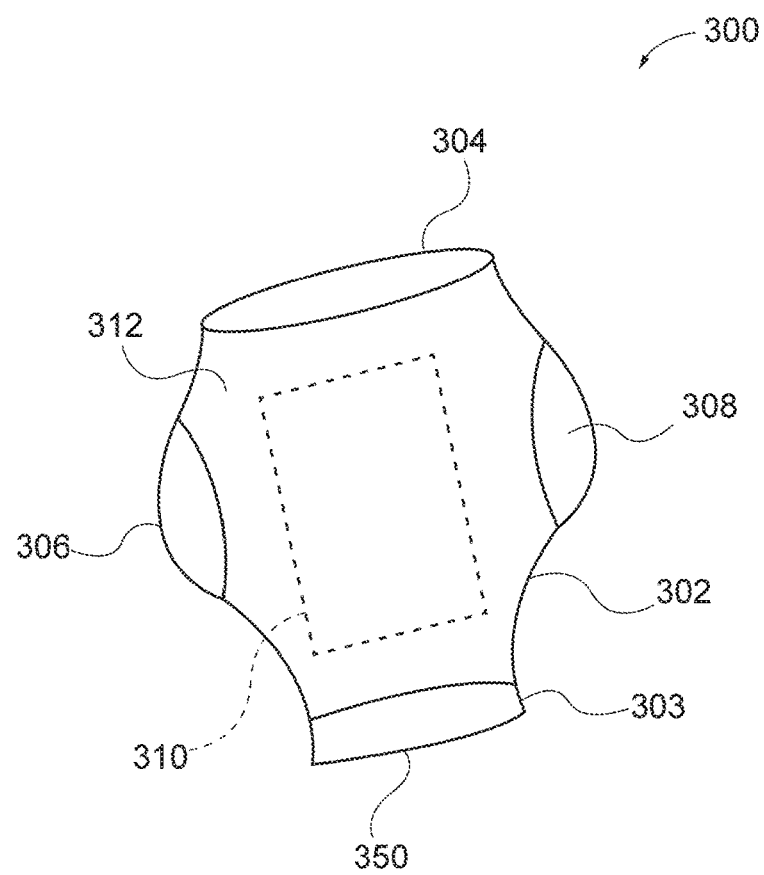
FIG. 11 is a perspective view of a manipulation device according to a third exemplary embodiment of the present invention.

An alternative embodiment of a manipulation device 300 according to a third exemplary embodiment of the present invention is shown in FIG. 11. Device 300 includes a glove 302 that has a finger opening 304 to allow a plurality of fingers (ie., four fingers) to be inserted therethrough, and two openings 306, 308 for thumbs. Openings 306, 308 are located on either side of finger opening 304. The two openings 306, 308 allow for glove 302 to be worn on either the right hand or the left hand of the user. A resistor assembly 310, similar to resistor assembly 102 described above, is sewn into palm portion 312 of glove 302 so that resistor assembly 310 is located at the user's thenar eminence and hypothenar eminence, regardless of which hand is inserted into glove 302. Resistor assembly 310 is electronically connected to a processor/transmitter 350 located in a wrist portion 303 of glove 302, similar to processor/transmitters 150, 250 described above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A manipulation and force measuring device comprising:
    a planar force sensing resistor;
    a protective material completely sandwiching the resistor;
    an outer material completely sandwiching the protective material;
    a first strap extending outwardly from the outer material, the first strap having one of a hook and loop fastener disposed thereon;
    a second strap extending outwardly from the outer material, distal from the first strap, the second strap having the other of the hook and loop fastener disposed thereon;
    a processor attached to one of the first strap and the second strap, the processor being electronically connected to the resistor; and
    a loop extending outwardly from the outer material, the loop being located proximate to the first strap.

2. The manipulation and force measuring device according to claim 1, wherein the device is sized to be worn on either a left hand or a right hand of a user.

3. The manipulation and force measuring device according to claim 2, wherein the loop is sized to allow a digit of the user to be inserted thereinto.

4. The manipulation and force measuring device according to claim 3, wherein the first strap and the second strap are each sufficiently long to allow the first strap to be releasably secured to the second strap around a wrist of the user.

5. The manipulation and force measuring device according to claim 4, wherein, when the first and second straps are secured to each other around a wrist and when a thumb is inserted into the loop, the resistor is located along a thenar eminence and hypothenar eminence of the user.

6. The manipulation and force measuring device according to claim 1, wherein the processor further comprises one of a visual display and a radio frequency transmitter.

7. A method of manipulating a patient, comprising the steps of:
    a. determining a hand on which to place the manipulation and force measuring device according to claim 1;
    b. inserting the thumb of the determined hand into the loop;
    c. securing the first strap to the second strap around the user's wrist;
    d. placing the manipulation and force measuring device at a desired location on the patient;
    e. applying a force to the location with the device; and
    f. viewing the amount of force being applied to the patient.

8. The method according to claim 7, further comprising, prior to step a., preselecting values for minimum force and maximum force to be applied in step e.

9. The method according to claim 8, further comprising, after step f., adjusting the amount of force being applied to the patient to maintain the applied force between the preselected values.

10. The method according to claim 7, wherein step f. further comprises recording the amount of applied force on the device.

11. The method according to claim 7, further comprising, between step e. and step f., transmitting a signal for the value of the amount of force being applied to a separate device.

* * * * *